United States Patent [19]

Edwards

[11] Patent Number: 5,989,559
[45] Date of Patent: Nov. 23, 1999

[54] BANANA PEEL EXTRACT COMPOSITION AND METHOD FOR EXTRACTION

[75] Inventor: Bobby Gene Edwards, Temple, Tex.

[73] Assignee: Delft Pharma International, Ogden, Utah

[21] Appl. No.: 09/015,537

[22] Filed: Jan. 29, 1998

[51] Int. Cl.$^6$ .............................. A61K 35/78; A61K 7/42; A61K 31/60; A61K 31/075

[52] U.S. Cl. ..................... 424/195.1; 424/59; 424/78.02; 424/78.05; 514/159; 514/715; 514/720; 514/886; 514/887; 514/969

[58] Field of Search .................................. 424/195.1, 59, 424/78.02, 78.05; 514/159, 715, 717, 720, 826, 886, 887, 906, 969; 426/49, 534, 542, 599, 655, 425, 431, 478, 489, 495

[56] References Cited

U.S. PATENT DOCUMENTS

| | | | |
|---|---|---|---|
| 4,670,463 | 6/1987 | Warren et al. | 514/464 |
| 4,921,709 | 5/1990 | Solé | 426/49 |

OTHER PUBLICATIONS

Shayne C. Gad, Brendan J. Dunn, Donald W. Dobbs, Christopher Reilly, and Robert D. Walsh, "Development and Validation of an Alternative Dermal Sensitization Test: The Mouse Ear Swelling Test (MEST)," Toxicology and Applied Pharmacology 84, 93–114 (1986).

Internet publication entitled "Unleashing the Power of the Banana Peel," Internet website for EXOREX™. Applicant first became aware of this internet publication on Dec. 15, 1997. Applicant is unaware when it was first available.

Internet publication entitled "Treatment for Psoriasis and Eczema" Applicant first became aware of this internet publication on Dec. 15, 1997. Applicant is unaware when it was first available.

Internet publication entitled "Exorex New Breakthrough Psoriasis Medication Launched" Applicant first became aware of this internet publication on Dec. 15, 1997. Applicant is unaware when it was first available.

Internet publication entitled "IMX Pharmaceuticals Signs Ecked Drug Stores for National Distribution of Exorex" Applicant first became aware of this internet publication on Dec. 15, 1997. Applicant is unaware when it was first available.

Newspaper article entitled "Banana Peel Cure Probably All in the Head." Applicant first became aware of this publication on Dec. 3, 1997. Applicant is unaware when it was first available.

*Primary Examiner*—Leon B. Lankford, Jr.
*Assistant Examiner*—Christopher R. Tate
*Attorney, Agent, or Firm*—Workman, Nydegger & Seeley

[57] ABSTRACT

An extract composition derived from the peel of a banana and the method for producing the extract composition. An aqueous solvent is combined with the peel of a banana. If the banana is unripe, a base is also added. The mixture is homogenized and allowed to react at least until a black supernatant appears. The entire slurry is filtered. The resulting extract is used alone or combined with a cream or ointment. Medicinal benefits of the extract include relief from pain, swelling, itching, bruising, wrinkles, and sunburn.

15 Claims, No Drawings

BANANA PEEL EXTRACT COMPOSITION AND METHOD FOR EXTRACTION

BACKGROUND OF THE INVENTION

1. The Field of the Invention

The present invention is directed generally to extraction methods, and more specifically to methods for extracting compounds from bananas.

2. The Relevant Technology

The common banana, scientifically known as *Musa sapientum*, is a tropical fruit grown in the western hemisphere. Primarily viewed as a food source, the banana has fleshy inside portion surrounded by an outer, typically yellow, peel. The fleshy inside portion, or pulp, is edible when raw, and the peel is usually discarded. When ripe, bananas have a deep yellow rind spotted with brown, and a creamy pulp which is easily digested. Bananas are rich in carbohydrates and contain relatively large amount of vitamins A, B and C and the minerals potassium and phosphorous.

The banana has value in addition to being a food source. The fruit producing tree contains fiber which is used in the production of paper and twine. The peel and pulp have also been utilized to obtain banana essences, which are solutions of aromatic components, essentially free of sugars and solid constituents. Banana essences have been obtained by homogenizing the pulp of a ripened banana, or by an extensive separation and extraction process of the peel.

Some cultures believe that the banana peel provides pain relief, especially from headache pain. However, experts in the field have maintained that there is nothing that is absorbed through the skin from a banana peel that has any effect on a headache. The experts argue that any relief experienced is probably a placebo effect.

SUMMARY AND OBJECTS OF THE INVENTION

It is an object of the present invention to provide improved and simplified methods for extracting desired substances from banana peels.

Yet another object of the invention is to provide medicinal uses for a banana peel extract composition.

It is another object of the invention to provide improved treatments for arthritis, inflammation, sunburn, and the like with the use of a banana peel extract composition.

These and other objects and features of the present invention will become more fully apparent from the following description and appended claims, or may be learned by the practice of the invention as set forth hereinafter.

To achieve the forgoing objects, and in accordance with the invention as embodied and broadly described herein, the present invention relates to new and useful methods for extracting beneficial substances from banana peels. Specifically, the invention is directed to a simplified extraction method which releases rare and unexpected compounds from the peel of a ripened banana. In one embodiment, banana peels are combined with 70% isopropyl alcohol, and blended into a slurry. The slurry is left to react for a period of time wherein a yellow supernatant forms at the top. This yellow supernatant changes to amber and then to an opaque black as the reaction proceeds. The entire slurry is then filtered and any solid material is discarded. Another filtration step yields the banana extract of the present invention.

Alternatively, unripened banana peels may be utilized in accordance with the method of the present invention. Unripened banana peels necessitate an additional step at the reaction stage: a base, such as sodium hydroxide or sodium bicarbonate, is added to the slurry.

DETAILED DESCRIPTION OF THE PREFERRED EMBODIMENTS

Extraction processes have been performed to extract banana essence from the otherwise discarded peel. In the conventional process disclosed in U.S. Pat. No. 4,921,709 by Solé, the yellow outer layer of the peel must be separated from the white inner layer including the white inner fibrils connecting the peel to the pulp. After separation, this white inner layer is digested with an enzyme to cause it to evolve into liquid and solid portions. During digestion, volatile components comprising banana essence are recovered by suction and condensation.

In contrast, the present invention is directed to the discovery that a simplified method of extraction from the peel of a banana provides new and useful compositions, without the extensive separation and enzyme digestion required by the conventional process. Specifically, certain rare and unexpected components are released from the banana peel in the form of an extract. The extract, when used for medicinal purposes is found to have the properties of an analgesic, an anti-inflammatory, and a smooth muscle relaxant. The extract also has been found to absorb ultraviolet light. It has also been useful in the treatment of sunburn when applied in the form of an ointment.

A preferred method in accordance with the present invention includes the following steps. First, banana peels are obtained such as by removing them from the banana fruit. It is preferable that the bananas are significantly ripe or "oxidized," e.g., the banana peels are brown, or even black. The stems are preferably removed and the peels are washed in water.

Next, the peels are coarsely chopped and placed in a solvent. 70% isopropyl alcohol, at a preferred ratio of approximately 1 gram of peel per about 4.5 ml of isopropyl alcohol is preferred. Alternatively, other alcohols, preferably in aqueous solution, can be utilized in place of the isopropyl alcohol. By way of illustration only, examples of alternative alcohol solvents include ethanol, propanol, or methanol in a peel to solvent ratio substantially similar to that of the 70% isopropyl alcohol.

The entire mixture is homogenized in a blender. The homogenized mixture, or "slurry," is then transferred to a reaction tank. Preferably, the surface of the reaction tank is left indirectly open to allow air on the liquid surface. The slurry is agitated periodically to disrupt any separation of the masticated peel from the isopropyl alcohol solvent. Agitation of the slurry is preferably performed by using a magnetic stir bar at the bottom of the reaction tank, by mixing the slurry with impellers, pumps, a mixing paddle, or by any other suitable manner which will expose the masticated peel to the solvent.

The slurry is left at room temperature and allowed to react for at least about 3 hours to about 48 hours or more. During the reaction time, the peel will settle and a yellow supernatant will appear at the top of the reaction tank. As the reaction continues, this yellow transparent liquid turns from yellow to amber to an opaque black liquid, which serves as an indicator that the reaction is substantially complete.

After completion of the reaction step, the entire slurry is then grossly filtered through screen mesh. The solid material collected in the screen mesh is discarded. The filtrate is further filtered through paper basket filters. Alternatively, the filtrate is filtered through flat paper filters supported by screen mesh. Preferably pressure, such as in the form of pneumatic or mechanical pressure, is applied to obtain the last remnants of the extract from the filter.

A sample is tested in a spectrophotometer at 370 nm using 70% isopropyl alcohol, or the solvent utilized in the extraction method, as the zero blank. The preferred optical density of the sample has been discovered to be about 2.0. At this optical density, it has been demonstrated that certain medicinal activity is maximized. The precise medicinal activity provided by an extract composition produced in accordance with the present invention will be illustrated in the examples to follow hereinbelow.

In an alternative embodiment of the present invention, the extraction method is performed with the use of non-ripe banana peels, which necessitates the additional step of adding a highly basic solution to the mixture of isopropyl alcohol and banana peel. In one embodiment, food grade sodium bicarbonate is added at about 3–10 grams per 100 ml of isopropyl alcohol used. Alternatively, sodium hydroxide is used in place of the sodium bicarbonate. It should be appreciated that other bases may be used in accordance with the method of the present invention. An indicator that the base is working is when yellow supernatant changes from clear yellow to opaque black. The use of an added base to obtain a basic pH is not necessary if the banana peels are brown or black as in the case of over-ripe bananas.

It has also been shown by the investigations associated with the present invention that the use of an acid, such as acetic acid, delays natural oxidation. In turn, there is no appearance of the extract components and thus no appreciable medicinally active material in an acidic solution. In fact, the extraction process can be controlled by manipulating the pH. In acidic solutions, even ripened banana peels may not produce medicinally active extracts. And in highly basic solutions, the rate at which the extract reaches an optical density of about 2.0 at 370 nm, and thus maximized medicinal activity, can be increased. Thus, reaction times of less than about 3 hours are achieved in highly basic solution.

In the investigations associated with the present invention, extensive spectrophotometric tests were performed to arrive at the preferred optical density described above. The tests were performed in an ultimately successful attempt to discover a means to detect the presence of active components in the banana peel extract. See, e.g., Examples A and B, below. Further, studies were performed to determine the acid-base relationship of the extract as detailed in Example C, below. Characterization of the components of the extract was also performed, the results of which are detailed in Example D and Table 3, below.

EXAMPLE A

*Musa sapientum* extracts were made from commercially purchased bananas in accordance with the method of the present invention detailed above. The bananas were approximately 25 cm long. Two different extracts were made: Extract #1 employed the use of peels from 2 bright yellow (non-oxidized) bananas; Extract #2 used the peels from blackened, over-ripe (oxidized) bananas. For each extract, the peels were minced and placed in 200 ml of 70% isopropyl alcohol, and then subjected to high speed blending in a commercial blender. The resulting slurries were left exposed to the air over night, and then filtered through Whaltman #1 filter paper.

Using a Cecil 1020 spectrophotometer, and 70% isopropyl alcohol as the zeroing blank, samples of both extracts were read at 660 nm, 406 nm, and 370 nm. Each extract was then filtered through a 0.2 micron filter, and samples were then remeasured at the same wavelengths. The results are illustrated in Table 1, below.

TABLE 1

| Wavelength | Blank | Extract #1 (Non-Oxid.) | Extract #1 (Non-Oxid) + Filt. | Extract #2 (Oxid) | Extract #2 (Oxid) + Filt |
|---|---|---|---|---|---|
| 660 nm | 0 | 0.019 | 0.008 | 0.083 | 0.035 |
| 406 nm | 0 | 0.464 | 0.407 | 1.342 | 1.196 |
| 370 nm | 0 | 1.074 | 1.058 | 2.055 | 1.946 |

The difference in compositions between the two extracts is best differentiated and indicated at 370 nm, although 406 nm also effectively distinguishes the two extracts. These results optically illustrate that the Extract #2 from oxidized peels contains optically measurable components that Extract #1 does not contain.

It was further determined utilizing samples of the two extracts that Extract #2 provided relief from pain and swelling when rubbed on an individuals painful and swollen hands. Extract #1 did not provide any such relief. Therefore, it is believed that the optically measurable difference is indicative of the medicinally active components of the extract.

EXAMPLE B

Another investigation was performed to determine whether any other adsorption peaks were achieved which could be employed to differentiate the oxidized, active extract, from the non-oxidized, inactive extract. Extracts from oxidized and non-oxidized bananas were prepared as described in Example A, above. The samples were tested via a Cecil 1020 spectrophotometer at wavelengths from 250 nm to 650 nm. Disposable cuvettes were utilized, and 70% isopropyl alcohol was used to calibrate the spectrophotometer at each wavelength. Once again, approximately 370 nm provided the optimal differentiation between the non-oxidized and oxidized extract samples.

EXAMPLE C

Banana peel extract utilizing partially oxidized banana peels were made in accordance with the method of the present invention described above. Samples of the extract were placed in two aliquots of 3 ml each. 0.1 ml of 0.1 N HCl was added to one aliquot; 0.1 ml of 0.1 N Sodium bicarbonate was added to the other. Each sample was read at 370 nm at various intervals, the results of which are illustrated in Table 2, below.

TABLE 2

| Time | HCl Sample O.D. | Sodium Bicarbonate Sample O.D. |
|---|---|---|
| 0 min | 1.268 | 1.232 |
| 1 min | 1.248 | 1.282 |
| 2 min | 1.248 | 1.290 |
| 3 min | 1.246 | 1.294 |
| 5 min | 1.204 | 1.512 |
| 7 min | 1.204 | 1.516 |
| 8 min | 1.204 | 1.516 |
| 10 min | 1.204 | 1.518 |
| 12 min | 1.204 | 1.550 |
| 25 min | 1.204 | 1.562 |
| 35 min | 1.202 | 1.864 |
| 120 min | 1.202 | 3.0 |

The results of this investigation illustrate that the addition of acid prevents the time-increase of optical density, and thus activity, of the extract. Further, addition of a base greatly facilitates the reaction. This acid-base relationship thus provides control to the extraction process.

EXAMPLE D

Characterization of the components of an extract composition derived from performance of the preferred method detailed hereinabove, was performed at the Georgia Institute of Technology. With the information discovered with respect to the pH and the UV adsorption at 370 nm of the present invention, it was possible to make an extract composition with no medicinal activity with the use of yellow, also described as "non-oxidized," bananas to compare with a medicinally active extract composition.

For each extract composition, active and inactive, about 20 ml was reduced via rotary evaporation to about 2 ml. This solution was then diluted to 5 ml with distilled water, and then extracted with 20 ml diethyl ether three times. The combined ether extracts were dried over magnesium sulfate, filtered and reduced to about 2 ml via rotary evaporation. The resulting solution was transferred to a vial for gas chromatography (GC)/mass spectrometry (MS) analysis. About 2 ml of the aqueous solution was also transferred to a vial for GC/MS analysis.

The GC parameters were as follows: HP6890 GC, injector temp of 250° C., initial oven temperature of 100° C., ramping to 250° C. at a rate of 15 deg/min. The column was an HP 19091K-413 capillary etc.

The results of the characterization are presented in Table 3, herein below.

TABLE 3

| Sample | Retention Time | Material | % of Total |
|---|---|---|---|
| Active Ether | 4.0 | Elemicin | 0.9 |
|  | 6.2 | Isopropyl mysistate | 4.7 |
|  | 6.7 | 3,3,5-trimethylcyclohexyl salicylate | 2.2 |
|  | 6.8 | Methyl 14-methylpentadecanoate | 3 |
|  | 7 | palmitic acid | 2.5 |
|  | 7.1 | dibutyl phthalate | 11 |
|  | 7.4 | isopropyl pamitate | 2.4 |
|  | 7.8 | methyl 9,12-octadecadienoate | 2.6 |
|  | 7.9 | methyl 9,12,16-octadecatrienoate | 2.1 |
|  | 8 | lineoleic acid | 6.2 |
|  | 8.1 | ethyl linoleolate | 7.4 |
|  | 9.1 | tryoctylamine | 5.7 |
|  | 11.8 | Bis(2-ethylhexyl)phthalate | 21.1 |
| Active Water | 7 | Palmitic acid | — |
| Inactive Ether | 4.4 | Butylated hydroxytoluene | — |
|  | 7.1 | dibutyl phthalate | — |
|  | 11.9 | Bis(2-ethylhexyl)phthalate | — |
| Inactive water | — | none identified | — |

A compound never before detected in banana peels was discovered at a retention time of 6.7 min. This compound was characterized as 3,3,5-trimethylcyclohexyl salicylate, and was not present in the inactive sample.

It is theorized that the 3,3,5-trimethylcyclohexyl salicylate contributes to the medicinal activity demonstrated by the extract composition. Thus, it is believed that an increase in the percent of this compound by weight of the composition will increase the medicinal activity of the composition.

Further, the rare compound known as elemicin is believed to cause a euphoric feeling. This compound has been isolated in spices (nutmeg) but was not expected to be found in the banana peel or extract therefrom.

A preferred extract composition in accordance with the present invention comprises a range of at least about 1.7% to about 2.7% or more of 3,3,5-trimethylcyclohexyl salicylate, and a range of about 0.4% to about 1.4% of elemicin by weight of the composition.

A more preferred extract composition comprises at least about 2.2% 3,3,5-trimethylcyclohexyl salicylate, and about 0.9% elemicin by weight of the composition.

The fatty acids are naturally occurring penetrants. In turn it is believed that these help deliver the active compounds to the painful site.

The present invention is also directed to the use of the medicinally active extract. As it is used herein, an "effective amount" means the amount of extract which when applied or utilized provides a desired effect. Various effects of the active extract components have been characterized in experimental studies, the results of which are included herein below. Yellow extract, such as from yellow bananas, was found to have no appreciable effect.

The extract composition has shown promising pharmaceutical value as a topical medicament. In one embodiment of the present invention, the relief from the cream extract was found to be intensified if reapplied after 5 minutes, and again in an hour. Further, at least one internal use for the extract composition has been evaluated.

In a preferred embodiment of the present invention, about 20 to about 30 ml of the extract of the present invention were mixed with about 16 ounces of "UnaVet udder cream," which is a proprietary cream base manufactured by UnaVet of Kansas City, Mo. It should be appreciated that other creams, ointments, lotions, oils, and the like can be used in accordance with the present invention as a carrier for the extract composition.

The extract-cream combination described above was utilized with the following results:

EXAMPLE E

Anti-inflammatory studies were performed using the "Mouse Ear Swelling Test." Prior to testing, the mice were measured to affirm that there was no significant difference in ear thickness from left to right ear. The mice were divided into 4 groups with ten mice per group. The left ear of each mouse was left untreated. The right ear of each mouse was treated with croton oil at 5.0% in acetone to provide an inflammatory response. The right ear of each mouse was then treated according one of four protocols. Group 1 received no additional treatment. Group 2 was treated with cream alone. Group 3 was treated with the extract of the present invention in alcohol. Group 4 was treated with the extract cream combination. After 24 hours the ears were measured. The results of this study are listed in Table 4, below.

TABLE 4

| Group # | Mouse Ear | Measurement | % Difference |
|---|---|---|---|
| Group 1 | Left Control | 2.57 |  |
| Group 1 | Right Control | 3.19 | 23.76% |
| Group 2 | Left Cream | 2.43 |  |
| Group 2 | Right Cream | 2.92 | 20.15% |
| Group 3 | Left Extract | 2.48 |  |
| Group 3 | Right Extract | 2.44 | −1.7% |
| Group 4 | Left Extract Cream | 2.43 |  |
| Group 4 | Right Extract Cream | 2.73 | 12.57% |

The results indicate that the extract alone and when combined with a cream has anti-inflammatory properties. The swelling was completely reduced after 24 hours in the mice treated with extract by itself.

EXAMPLE F

Extract cream was rubbed onto the skin of a fair, white male, age 48 who sunburns easily. The UV index outside was 9, and the temperature was 85° F. Exposure was direct for 5 hours with no resultant discomfort or redness.

On the next day, with the same temperature and UV index, the same fair, white male was exposed to direct sunlight for 3 hours without using the cream extract, resulting in severely sunburned skin. However, the extract cream was rubbed on the burned skin which relieved the pain up to 4 hours before a new application was needed. No blistering or peeling was experienced, despite the reported tendency of the participant's skin to do so.

EXAMPLE G

Poison ivy was encountered by an individual who normally experienced significant pustules, intense itching and difficulty breathing upon any contact with poison ivy. Extract cream was applied to the skin of the individual and the itching stopped instantly. The pustules appeared, but in a more mild form than typically experienced by the individual. The mild pustules were completely resolved in seven days. The extract cream further controlled the difficulty in breathing typically experienced by the individual.

EXAMPLE H

An individual was exposed on two different occasions to poison oak. Application of the cream was effective in controlling the itch and lesions associated with poison oak exposure for this individual on both occasions.

EXAMPLE I

An individual experienced chronic pain in her hand due to a prior, serious break. This pain was so severe that two and a half years following the break, the individual still could barely write or work. After applying the extract cream to the sore hand, the individual experienced almost immediate pain relief.

EXAMPLE J

The individual from Example I, above, also experienced significant wrinkling in her hand. After overnight application of the extract cream, the wrinkles disappeared and the skin was soft and appeared youthful.

EXAMPLE K

An individual underwent extensive neck surgery. The incision was very deep and extended from under his chin to his collar bone. The pain was severe and prevented the individual from utilizing his neck in the manner required for singing. After application of the extract cream to the scar, the individual experienced relief from the soreness of the incision. Regular use of the extract cream on the scar provided enough relief to permit the individual to continue singing in his church choir.

EXAMPLE L

An individual experienced sore muscles due to over-exertion. The soreness in her leg muscles was eliminated after she rubbed the extract cream into her legs.

EXAMPLE M

The individual from Example L, above, utilized the extract cream on her muscles prior to exertion. She did not experience any post-exertion muscle soreness.

EXAMPLE N

An individual experienced relief from insect bites with use of the extract cream. When rubbed on an insect bite almost immediately and at about two hour intervals after the bite, the extract cream prevented the bite from swelling or becoming painful and irritating. When rubbed on an insect bite after it had begun to swell and itch, the extract cream eliminated the itch and helped to decrease the swelling and redness.

EXAMPLE O

One individual experienced pain in her toe, knee, hip, and lumbro-sacral joints. After rubbing the extract cream into these areas, the individual experienced relief from her pain. The individual noted that the toe joint required only one application of the cream and pain was alleviated completely in about twenty minutes.

EXAMPLE P

An individual suffering from carpal tunnel syndrome experienced soreness and swelling in her right arm. She also experienced numbness in her right hand. After she applied extract cream to her right wrist, the swelling and the pain subsided, and the feeling returned to her hand.

EXAMPLE Q

An individual suffering from an arthritic right ankle experienced pain to the extent that walking was difficult. After regular application of the extract cream to the ankle, the individual experienced significant relief in about a week.

EXAMPLE R

A seventy-four year old woman was in a serious car accident over thirty years ago. The accident left her hospitalized for a long period of time and caused extensive damage to her knees. About five years ago, she refused against the advice of a doctor to have knee replacement surgery. When this individual was ambulatory, she was in significant pain, and could not bend her knees, but walked with "peg-legs." Her legs were very large and disfigured, very stiff, and basically unable to bend. Some she could not walk at all. Extract cream was rubbed on both of her knees. After about 5 to 10 minutes, the individual was able to bend her legs while in a seated position. She then was able to stand up and walk with improved mobility in her knees. The individual noted that some amount of pain remained in her knees, but a significant amount had been relieved upon application of the extract cream. After regular daily use of the cream for a week, the size of her knees was reduced considerably.

EXAMPLE S

An individual suffered for over ten years from a very painful and debilitating arthritic condition in the joints in her hands. After applying the extract cream by massaging it into her hands twice daily, the individual experienced pain relief and improved dexterity.

EXAMPLE T

An individual was plagued with dark under eye circles which required substantial cover-up. The extract cream was applied to dark under eye circles. After such application, the darkness of the under eye circles was significantly reduced.

EXAMPLE U

An individual reported reduction in the longevity of bruising when the extract cream was applied around a bruised area. A marked improvement in severe bruising was reported after only a day and a half. It is believed from this result that the cream may also prevent the vascular damage associated with bruising.

EXAMPLE V

Individuals utilizing the extract cream noted that in addition to the benefits detailed in the previous examples above, the extract cream provided moderate euphoric effects.

EXAMPLE W

A 10 year old female mixed breed dog experienced an allergic reaction. Her nose, face, and ears swelled up. Extract cream was rubbed on these areas in one application. Within 24 hours, the swelling was completely gone and no further allergy symptoms were apparent.

EXAMPLE X

Banana peel extract in accordance with the present invention was tested at the University of Wisconsin wherein it was found to demonstrate smooth muscle relaxation on guinea pig trachea rings. These results favor utilized the extract in the treatment of asthma.

In this study, female Hartley guinea pigs were obtained from Harlan Sprague Dawley and actively sensitized by intraperitoneal injection of chicken egg albumen. Baths were filled with 10 ml of Krebs solution, maintained at 37° C., and aerated with a mixture of 95% oxygen and 5% carbon dioxide. Tracheal rings were prepared by gently removing the trachea, trimming off excess tissues, and cutting into four cross-sections about 3–4 mm in length. Tension was measured using a Grass FT-03 isometric transducer and a Grass 7-E polygraph. An optimal tension of 1.5 gm was imposed on the tissues throughout 1 hour of equilibration. During this time, the Krebs solution in the baths was changed at 15 min. intervals.

To initiate contraction, ovalbumin was added to the baths at a concentration of 0.01 µg/ml. A control tracheal ring was challenged with ovalbumin alone for comparison of the natural relaxation curve over time. The extract was added at peak contraction (3 minutes following ovalbumin challenge). To produce dose response curves, increasing doses of the extract (0.1, 1.0, 5.0%) were added. The response to each dose was allowed to stabilize for each treatment (up to 3 minutes at the same tension) before addition of the next dose. Following stabilization of the response to the final dose, papaverine was added to induce 100% relaxation. The results indicate that the extract exhibits significant smooth muscle relaxation, especially at the 5.0% dosage.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A topically applied medicinal composition, said composition comprising:
    a) 3,3,5-trimethylcyclohexyl salicylate in an amount by weight of at least about 1.7% of the composition; and
    b) elemicin in an amount by weight of at least 0.4% of the composition.
2. The composition as recited in claim 1, further comprising isopropyl mysistate in an amount by weight of about 4.7% of the composition.
3. The composition as recited in claim 1, further comprising methyl 14-methylpentadecanoate in an amount by weight of about 3% of the composition.
4. The composition as recited in claim 1, further comprising isopropyl pamitate in an amount by weight of about 2.4% of the composition.
5. The composition as recited in claim 1, further comprising methyl 9,12-octadecadienoate in an amount by weight of about 2.6% of the composition.
6. The composition as recited in claim 1, further comprising methyl 9,12,16-octadecatrienoate in an amount by weight of about 2.1% of the composition.
7. The composition as recited in claim 1, further comprising linoleic acid in an amount by weight of about 6.2% of the composition.
8. The composition as recited in claim 1, further comprising ethyl linoleate in an amount by weight of about 7.4% of the composition.
9. The composition as recited in claim 1, further comprising tryoctylamine in an amount by weight of about 5.7% of the composition.
10. The composition as recited in claim 1, further comprising a carrier material.
11. The composition as recited in claim 10, wherein said carrier material is a cream.
12. The composition as recited in claim 10, wherein said carrier material is a lotion.
13. The composition as recited in claim 10, wherein said carrier material is an ointment.
14. The composition as recited in claim 10, wherein said carrier material is an oil.
15. A topically applied medicinal composition from at least one banana peel, said composition comprising 3,3,5-trimethylcyclohexyl salicylate; and elemicin in therapeutically effective amounts.

* * * * *

UNITED STATES PATENT AND TRADEMARK OFFICE
CERTIFICATE OF CORRECTION

PATENT NO. : 5,989,559
DATED : November 23, 1999
INVENTOR(S) : Bobby Gene Edwards It is certified that error appears in the above-identified patent and that said Letters Patent is hereby corrected as shown below:

<u>Title page,</u>
Item [73], Assignee, delete "Delft Pharma International, Ogden, Utah"

Signed and Sealed this

Sixteenth Day of September, 2003

JAMES E. ROGAN
*Director of the United States Patent and Trademark Office*